United States Patent
Rebbeck et al.

(10) Patent No.: US 6,174,684 B1
(45) Date of Patent: Jan. 16, 2001

(54) CYP3A4 NFSE VARIANT AND METHODS OF USE THEREFORE

(75) Inventors: Timothy R. Rebbeck, Wynnewood; Carolyn A. Felix, Ardmore, both of PA (US)

(73) Assignees: Trustees of the University of Pennsylvania; Childrens Hospital of Pennsylvania, both of Philadelphia, PA (US)

(*) Notice: Under 35 U.S.C. 154(b), the term of this patent shall be extended for 0 days.

(21) Appl. No.: 09/372,339

(22) Filed: Aug. 11, 1999

Related U.S. Application Data

(60) Provisional application No. 60/096,586, filed on Aug. 14, 1998.

(51) Int. Cl.[7] .............................. C12Q 1/68; C12P 19/34; C07M 21/00

(52) U.S. Cl. ........................ 435/6; 435/91.1; 435/91.2; 536/23.1; 536/24.3

(58) Field of Search ............................ 435/6, 91.2, 91.1; 536/231, 24.3

(56) References Cited

PUBLICATIONS

Beahrs et al., *Manual for Staging of Cancer*, 4th edition, 185–186; Philadelphia: JP Lippincott, 1992.
Cavalieri, et al., "Molecular origin of cancer: Catecholestrogen–3,4–quinones as endogenous tumor initiators", 1997 *Proc. Natl Acad. Sci. USA* 94:10937–10942.
Demple et al., "Repair of Oxidative Damage to DNA: Enzymology and Biology", *Annu. Rev. Biochem.* 1994 63:915–948.
Felix, et al., "Panhandle Polymerase Chain Reaction Amplifies MLL Genomic Translocation Breakpoint Involving Unknown Partner Gene", *Blood* 1997 90:4679–4786.
Felix, et al., "The p53 Gene in Pediatric Therapy–Related Leukemia and Myelodysplasia", *Blood* 1996 87:4376–4381.
Felix, et al., "All–1 Gene Rearrangements in DNA Topoisomerase II Inhibitor–Related Lukemia in Children", *Blood* 1995 85:3250–3256.
Felix, et al., "Characterization of Immunoglobulin and T–Cell Receptor Gene Patterns in B–Cell Precursor Acute Lymphoblastic Leukemia of Childhood", *Blood* 1995 85:3250–3256.
Ganguly, et al., "Conformation–sensitive gel electrophoresis for rapid detection of single–base differences in double–stranded PCR products and DNA fragments: Evidence for solvent–induced bends in DNA heteroduplexes", *Proc. Natl Acad. Sci. USA* 1993 90:10325–10329.
Giovannucci, et al., "The Cag repeat within the androgen receptor gene and its relationship to prostate cancer", *Proc. Natl Acad. Sci. USA* 1997 94(7):3320–3323.
Gleason, D.F., "Histologic Grading and Clinical Staging of Prostatic Carcinoma", *The Veteran's Administration Cooperative Urologic Research group. In Tannenbaum M. (ed.) Urologic Pathology: The Prostate* , pp. 171–198 Philadelphia: Lea and Febiger, 1997.
Gu Y., "The t(4;11) Chromosome Translocation of Human Acute Leukemias Fuses the ALL–1 Gene, Related to Drosophila trithorax, to the AF–4 Gene", 1992 71:701–708.
Hashimoto, et al., "Gene structure of CYP3A4, an adult–specific form of cytochrome P–450 in human livers, and its transcriptional control", *Eur. J. Biochem.* 1993 218:585–595.
Inoue, et al., "Assignment of the Human Cytochrome P–450 Nifedipine Oxidase Gene (CYP3A4) to Chromosome 7 at Band q22.1 by Fluorescence in Situ Hybridization", *Jpn. J. Hum. Genet.* 1992 37:133–138.
Ingles, et al., "Association of Prostate Cancer Risk With Genetic Polymorphisms in Vitamin D Receptor and Androgen Receptor", 1997 *J. Nat. Cancer Inst.* 89(2):166–170.
Kingma, et al., "Abasic Sites Stimulate Double–stranded DNA Cleavage Mediated by Topoisomerase II", *J. Biol. Chem.* 1995 270:21441–21444.
Kingma, et al., "Apurinic Sites Are Position–specific Topoisomerase II Poisons", *J. Biol. Chem.* 1997 272:1148–1155.
Kingma, et al., "Spontaneous DNA Damage Stimulates Topoisomerase II–mediated DNA Cleavage", *J. Biol. Chem.* 1997 272:7488–4793.
Kingma, et al., "Spontaneous DNA Lesions Poison Human Topoisomerase II and Stimulate Cleavage Proximal to Leukemic 11q23 Chromosomal Breakpoints", *Biochem.* 1997 36:5934–5939.
Kleinbloesem, et al., "Variability in Nifedipine Pharmacokinetics and Dynamics: A New Oxidation Polymorphism in Man", *Biochemical Pharmacology* 1984 33:3721–3724.
Krokan, et al., "DNA glycosylases in the base excision repair of DNA", *Biochem.* 1997 325:1–16.
Li, et al., "Substrates of human hepatic cytochrome P–450 3A4", *Toxicology* 1995 104:1–8.
Megonigal, et al., "t(11;22)(q23;q11.2) in acute myeloid leukemia of infant twins fuses MLL with hCDCrel, a cell division cycle gene in the genomic region of deletion in DiGeorge and velocardiofacial syndromes", *Proc. Natl Acad. Sci. USA* 1998 95:6413–6418.
Megonigal, et al., "Panhandle PCR strategy to amplify MLL genomic breakpoints in treatment–related leukemias", *Proc. Natl Acad. Sci. USA* 1997 94:11583–11588.

(List continued on next page.)

Primary Examiner—Jeffrey Fredman
(74) *Attorney, Agent, or Firm*—Law Offices of Jane Massey Licata

(57) ABSTRACT

A nucleic acid sequence encoding a variant CYP3A4 gene is provided. Also provided are methods and kits for identifying individuals carrying a variant CYP3A4 gene with a heightened risk of developing or having prostate cancer or a decreased risk for developing treatment-related leukemias and identifying more effective and safer treatment regimes for individuals based upon their CYP3A4 genotype.

7 Claims, No Drawings

PUBLICATIONS

Murray, et al., "The Immunohistochemical Localization of Drug–Metabolizing Enzymes in Prostate Cancer", *J. Pathology* 1995 177:147–152.

Reichardt, et al., "Genetic Variability of the Human SRD5A2 Gene: Implications for Prostate Cancer Risk[1]", *Cancer Res.* 1995 55(18):3973–3975.

Relling, et al., "Multiplex PCR amplification from the CFTR gene using DNA prepared from buccal brushes/swabs", *AM. Soc. Pharmacol. Exp. Therapeut.* 1994 45:352–358.

Singer, et al., "What Structural Features Determine Repair Enzyme Specificity and Mechanism in Chemically Modified DNA?", *Chem. Res. Toxicol.* 1997 10:713–732.

Sun, et al., "Studies on the Catalytic Mechanism of Five DNA Glycosylases", *J. Bio. Chem.* 1995 270:19501–19508.

Waxman, et al., "Human liver microsomal steroid metabolism: identification of the major microsomal steroid hormone 6 beta–hydroxylase cytochrome P–450 enzyme", *Arch. Biochemical Pharmacology* 1998 263:242–436.

Wilkinson, G.R., "Cytochrome P4503A (CYP3A) Metabolism: Prediction of In Vivo Activity in Humans", *J. Pharmacokinet. Biopharm.* 1996 24:475–490.

Stratagene Catalog, p. 39.*

Relling et al, "o–demethylation of epipdophyllotoxins is catalyzed by human cytochrome p450 3A4", Mol. Pharm. 45:352–358.*

* cited by examiner

SEQUENCE LISTING

<160> NUMBER OF SEQ ID NOS: 6

<210> SEQ ID NO 1
<211> LENGTH: 1345
<212> TYPE: DNA
<213> ORGANISM: Homo sapiens

<400> SEQUENCE: 1

```
ctgcagtgac cactgcccca tcattgctgg ctgaggtggt tggggtccat ctggctatct      60
gggcagctgt tctcttctct cctttctctc ctgtttccag acatgcagta tttccagaga     120
gaagggcca ctctttggca aagaacctgt ctaacttgct atctatggca ggacctttga      180
agggttcaca ggaagcagca caaattgata ctattccacc aagccatcag ctccatctca     240
tccatgccct gtctctcctt taggggtccc cttgccaaca gaatcacaga ggaccagcct     300
gaaagtgcag agacagcagc tgaggcacag ccaagagctc tggctgtatt aatgacctaa     360
gaagtcacca gaaagtcaga aggatgcata gcagaggccc agcaatctca gctaagtcaa     420
ctccaccagc ctttctagtt gcccactgtg tgtacagcac cctggtaggg accagagcca     480
tgacagggaa taagactaga ctatgccctt gaggagctca cctctgttca gggaaacagg     540
cgtggaaaca caatggtggt aaagaggaaa gaggacaata ggattgcatg aagggatgg      600
aaagtgccca ggggaggaaa tggttacatc tgtgtgagga gtttggtgag gaaagactct     660
aagagaaggc tctgtctgtc tgggtttgga aggatgtgta ggagtcttct aggggggcaca    720
ggcacactcc aggcataggt aaagatctgt aggtgtggct tgttgggatg aatttcaagt     780
attttggaat gaggacagcc atagagacaa gggcaagaga gaggcgattt aatagattt     840
atgccaatgg ctccacttga gtttctgata agaacccaga acccttggac tccccagtaa     900
cattgattga gttgtttatg atacctcata gaatatgaac tcaaaggagg tcagtgagtg     960
gtgtgtgtgt gattctttgc caacttccaa ggtggagaag cctcttccaa ctgcaggcag    1020
agcacaggtg gccctgctac tggctgcagc tccagccctg cctccttctc tagcatataa    1080
acaatccaac agcctcactg aatcactgct gtgcagggca ggaaagctcc atgcacatag    1140
cccagcaaag agcaacacag agctgaaagg aagactcaga ggagagagat aagtaaggaa    1200
agtagtgatg gctctcatcc cagacttggc catggaaacc tggcttctcc tggctgtcag    1260
cctggtgctc ctctatctgt gagtaactgt tcaggctcct cttctctgtt tcttggactt    1320
ggggtcgtaa tcaggcctct ctttt                                          1345
```

<210> SEQ ID NO 2
<211> LENGTH: 1345
<212> TYPE: DNA
<213> ORGANISM: Homo sapiens

<400> SEQUENCE: 2

```
ctgcagtgac cactgcccca tcattgctgg ctgaggtggt tggggtccat ctggctatct      60
gggcagctgt tctcttctct cctttctctc ctgtttccag acatgcagta tttccagaga     120
gaagggccca ctcttttggca aagaacctgt ctaacttgct atctatggca ggacctttga    180
agggttcaca ggaagcagca caaattgata ctattccacc aagccatcag ctccatctca     240
tccatgccct gtctctcctt tagggggtccc cttgccaaca gaatcacaga ggaccagcct    300
gaaagtgcag agacagcagc tgaggcacag ccaagagctc tggctgtatt aatgacctaa     360
gaagtcacca gaaagtcaga aggatgcata gcagaggccc agcaatctca gctaagtcaa     420
ctccaccagc ctttctagtt gcccactgtg tgtacagcac cctggtaggg accagagcca     480
tgacagggaa taagactaga ctatgcccctt gaggagctca cctctgttca gggaaacagg    540
cgtggaaaca caatggtggt aaagaggaaa gaggacaata ggattgcatg aagggatgg     600 aaagtgccca ggggaggaaa tggttacatc tgtgtgagga gtttggtgag gaaagactct    660
aagagaaggc tctgtctgtc tgggtttgga aggatgtgta ggagtcttct aggggcaca    720 ggcacactcc aggcataggt aaagatctgt aggtgtggct tgttgggatg aatttcaagt    780
attttggaat gaggacagcc atagagacaa gggcaggaga gaggcgattt aatagatttt    840
atgccaatgg ctccacttga gtttctgata agaacccaga acccttggac tccccagtaa    900
cattgattga gttgtttatg atacctcata gaatatgaac tcaaaggagg tcagtgagtg    960
gtgtgtgtgt gattctttgc caacttccaa ggtggagaag cctcttccaa ctgcaggcag    1020
agcacaggtg gccctgctac tggctgcagc tccagccctg cctccttctc tagcatataa    1080
acaatccaac agcctcactg aatcactgct gtgcagggca ggaaagctcc atgcacatag    1140
cccagcaaag agcaacacag agctgaaagg aagactcaga ggagagagat aagtaaggaa    1200
agtagtgatg gctctcatcc cagacttggc catggaaacc tggcttctcc tggctgtcag    1260
cctggtgctc ctctatctgt gagtaactgt tcaggctcct cttctctgtt tcttggactt    1320
ggggtcgtaa tcaggcctct ctttt                                          1345

<210> SEQ ID NO 3
<211> LENGTH: 10
<212> TYPE: DNA
<213> ORGANISM: Homo sapiens

<400> SEQUENCE: 3
agggcaagag                                                            10

<210> SEQ ID NO 4
<211> LENGTH: 10
<212> TYPE: DNA
<213> ORGANISM: Homo sapiens

<400> SEQUENCE: 4
agggcaggag                                                            10

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 5
aacaggcgtg gaaacacaat                                                 20
```

```
<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 6
ctttcctgcc ctgcacag                                                    18
```

CYP3A4 NFSE VARIANT AND METHODS OF USE THEREFORE

INTRODUCTION

This application claims the benefit of priority from provisional patent application Ser. No. 60/096,586, filed Aug. 14, 1998.

This invention was supported in part by funds from the U.S. government (NIH Grant Nos. ES-08031 and IR29CA66140-04) and the U.S. government may therefore have certain rights in the invention.

FIELD OF THE INVENTION

The present invention relates to a nucleic acid sequence encoding a novel CYP3A4 variant, referred to herein as CYP3A4-V. CYP3A4 is a metabolizer of multiple drugs. Thus, identification of this polymorphism is believed to be useful in predicting susceptibility of individuals to a broad spectrum of diseases and/or treatments. For example, detection of this variant can be used to predict risk for development of prostate cancer in a patient. Detection of this variant can also be used to predict risk for development of treatment-related leukemia in a patient upon administration of an epipodophyllotoxin. Kits for detection of this variant are thus provided. Also provided in the present invention are methods of identifying more effective treatment regimes for individuals with prostate cancer and safer anticancer drugs which will not lead to treatment-related leukemia through the identification of individuals carrying CYP3A4 variants.

BACKGROUND OF THE INVENTION

Prostate cancer is the most commonly diagnosed nondermatologic cancer in the United States among men. It has been estimated that over 325,000 new cases of prostate cancer are diagnosed in the United States each year, with over 40,000 fatalities annually.

The etiology of prostate cancer involves the effects of androgens as well as inherited genotypes that regulate androgen metabolism. Candidate prostate cancer genes include those involved in androgen metabolism, such as the androgen receptor (Giovannucci et al. Proc. Natl Acad. Sci. USA 1997 94(7):3320–3; Ingles et al. J. Nat. Cancer Inst. 1997 89(2):166–170) or 5-α-reductase type II (Reichardt et al. Cancer Res. 1995 55(18):3973–5) genes. Additional candidates include members of the cytochrome P450 supergene family involved in androgen metabolism.

One member of this multigene family is CYP3A4, a gene involved in the oxidation of testosterone to 2β-, 6β-, or 15β-hydroxytestosterone (Waxman et al. Arch. Biochemical Pharmacology 1988 263:242–436). Substantial interindividual variability in metabolism of specific compounds by CYP3A4 has been reported (Kleinbloesem et al. Biochemical Pharmacology 1984 33:3721–3724), yet no genetic basis for this variability has been found. CYP3A4 protein has been reported to be expressed in only 61% of prostate tumors (Murray et al. J. Pathology 1995 177:147–152).

Second cancers are uncommon events occurring at a frequency of about 7% in survivors of primary malignant neoplasms. Leukemias are the major type of second cancers resulting from chemotherapy. There are two main forms of treatment-related leukemia, those with chromosome 5 and 7 monosomies induced by alkylating agents, and those with MLL gene translocations and other translocations related to DNA topoisomerase II inhibitors. Since only a minority of patients develop leukemia following chemotherapy, it has been suggested that differences in drug interactions with the host may be the predisposing factors (Boice et al. Proc. AACR 1997 38:645).

Genetic polymorphisms can account for large differences in the pharmacokinetics of chemotherapeutic agents, but metabolism of the majority is polygenetically determined and unimodally distributed. There is a 5- to 20-fold interindividual variability in drug clearance, which is a consequence of genetic and non-genetic factors. CYP3A-mediated first pass metabolism occurs after oral drug administration and has been suggested to contribute to the variability. CYP3A activity can also be modulated by inducers such as rifampin and anticonvulsants, inhibitors such as azole antifungal agents and macrolide antibiotics, by liver disease and by aging (Wilkinson, G. R. J. Pharmacokinet. Biopharm. 1996 24:475–490).

Epipodophyllotoxins are associated with leukemias characterized by translocation of the MLL gene at chromosome band 11q23 and other translocations. The epipodophyllotoxins, etoposide and teniposide and cyclophosphamide, ifosphamide, vinblastine and vindesine are substrates for metabolism by CYP3A.

A variant in the 5' promoter region of the CYP3A4 gene has now been identified. This polymorphism comprises an A→G transition in the nifedipine-specific response element (NFSE) of the gene. Detection of this polymorphism is useful as a biomarker in predicting prostate cancer and epipodophyllotoxin-induced leukemogenesis.

SUMMARY OF THE INVENTION

An object of the present invention is to provide a nucleic acid sequence encoding a variant of CYP3A4.

Another object of the present invention is to provide a method of identifying patients with heightened risk of developing or having prostate cancer which comprises obtaining a biological sample from the patient and testing for the presence of a nucleic acid sequence encoding a variant of CYP3A4 in the sample, wherein the presence of this variant is indicative of a heightened risk of the patient developing or having prostate cancer.

Another object of the present invention is to provide a method of identifying patients at risk for developing treatment-related leukemia upon administration of an epipodophyllotoxin which comprises obtaining a biological sample from the patient and testing the sample for the presence of wildtype CYP3A4 or a variant CYP3A4, wherein the presence of wildtype CYP3A4 is indicative of an increased risk of the patient developing treatment-related leukemia upon administration of an epipodophyllotoxin while the presence of variant CYP3A4 is indicative of a decreased risk of the patient developing treatment-related leukemia upon administration of an epipodophyllotoxin.

Another object of the present invention is to provide a kit for identifying patients with heightened risk of developing or having prostate cancer or decreased risk for developing treatment-related leukemia upon administration of an epipodophyllotoxin, wherein said kit comprises a means for detecting wildtype CYP3A4 or a variant CYP3A4 in a biological sample.

Another object of the present invention is to provide methods for identifying more effective treatment regimes for prostate cancer which comprises identifying individuals suffering from prostate cancer who carry a variant CYP3A4 gene and selecting a treatment regime which is more effective in the presence of the variant CYP3A4 gene.

Yet another object of the present invention is to provide a method of identifying safer anticancer treatments for a patient suffering from cancer which comprises identifying whether a patient carries wildtype CYP3A4 or a variant CYP3A4 and selecting a safer treatment regime for patients carrying wildtype CYP3A4 or individualizing treatment doses based on whether the CYP3A4 genotype is variant or wildtype.

DETAILED DESCRIPTION OF THE INVENTION

CYP3A4 (OMIM*124010, GenBank D11131, SEQ ID NO:1) is a member of the cytochrome P450 supergene family involved in the metabolism of numerous compounds including aflatoxin B1, steroid hormones such as testosterone and estrogen, and numerous drugs (Li et al. Toxicol. 1995 104:1–8). A variant in the 5' promoter region of the CYP3A4 gene has now been identified. This variant is referred to herein as CYP3A4-V (SEQ ID NO:2). This genetic variant has been found to disrupt a regulatory element upstream of CYP3A4. Specifically, CYP3A4-V comprises an A to G transition that alters the 10 base pair nifedipine-specific element located –287 to –296 base pairs from the transcription start site of CYP3A4. As a major metabolizer of hundreds of drugs, the applicability of this polymorphism to susceptibility of individuals to various treatments and/or diseases is believed to be quite broad.

For example, it has also now been found that prostate cancer patients who carry this variant allele have a higher clinical stage than patients who do not carry this variant. It is believed that CYP3A4-V genotype carriers may have decreased CYP3A4 activity, and thus decreased 2β-, 6β-, and 15β-testosterone oxidation. This decreased oxidation is believed to increase the bioavailability of testosterone for conversion to its intracellular mediator, dihydrotestosterone (DHT), the principal androgenic hormone involved in the regulation of prostate cell growth and function. Therefore, the CYP3A4 variant appears to be involved in androgen mediated prostate carcinogenesis, thereby influencing the presentation of prostate cancers.

Using a reference sample of 94 unselected, unrelated Caucasians with no history of cancer, 12 carriers of variant alleles were identified by CSGE analysis of the 5' regulatory region of the CYP3A4 gene. These subjects were confirmed by direct sequencing to be heterozygotes for an A to G transition mutation that alters the 10 bp (AGGGCAAGAG (SEQ ID NO:3) to AGGGCAGGAG (SEQ ID NO:4)) nifedipine-specific element (NFSE), located –287 to –296 bp from the transcription start site of the CYP3A4 gene (Hashimoto et al. Eur. J. Biochem. 1993 218:585–595). This variant CYP3A4 gene is referred to herein as CYP3A4-V. Three homozygous variant carriers were also identified in this reference panel by CSGE and confirmed to carry the same variant by direct sequencing. A randomly selected set of 12 of the 79 individuals inferred to be homozygous wild-type from CSGE were also sequenced. No nucleotide changes relative to the wild type sequence were detected in these individuals. Thus, the CYP3A4 variant allele frequency in the U.S. Caucasian population is estimated to be 9.6%, with an observed heterozygosity of 12.8%. The NFSE is a purine-rich element that has homology with the basic transcription element (BTE). The NFSE has been previously identified as a CYP3A4-specific element that is bound by nuclear proteins, and falls within a region required for CYP3A4 transcription in HepG2 cells (Hashimoto et al. Eur. J. Biochem. 1993 218:585–595).

Analyses were undertaken to evaluate the relationship of CYP3A4 genotypes with clinical characteristics of prostate tumors considering wild type homozygotes (CYP3A4-W) versus heterozygotes or homozygotes for the CYP3A4 variant (CYP3A4-V). There was no association of CYP3A4 genotype with PSA level at diagnosis in analysis of unadjusted PSA ($\chi^2$=0.22, P=0.637) or PSA adjusted for age and mode of prostate cancer detection ($\chi^2_1$=2.14, P=0.143). There was also no significant association of genotype with PSA level in any group defined by age at diagnosis or family history. Genotype was not associated with an earlier age at diagnosis in unadjusted analysis ($\chi^2_1$=1.12, P=0.290), or in analysis adjusted for mode of prostate cancer detection ($\chi^2_1$=0.71, P=0.399).

CYP3A4-V genotypes were overrepresented in tumors of higher stage and grade (Tables 1 and 2).

TABLE 1

Association of CYP3A4 Genotype with TNM Stage in 230 Incident Prostate Cancer Patients

| Age of Diagnosis | TNM Stage | Family History Negative | | Family History Positive | | Any Family History | |
|---|---|---|---|---|---|---|---|
| | | W | V | W | V | W | V |
| ≤63 years | T1a-T1c | 14 (88%) | 2 (12%) | 5 (71%) | 2 (29%) | 19 (83%) | 4 (17%) |
| | T2a-T2c | 31 (74%) | 11 (26%) | 17 (89%) | 2 (11%) | 48 (79%) | 13 (21%) |
| | T3 or T4 | 20 (87%) | 3 (13%) | 7 (100%) | 0 (0%) | 27 (90%) | 3 (10%) |
| | | FET P = 0.401 | | FET P = 0.369 | | FET P = 0.411 | |
| >63 years | T1a-T1c | 20 (95%) | 1 (5%) | 6 (100%) | 0 (0%) | 26 (96%) | 1 (4%) |
| | T2a-T2c | 40 (87%) | 6 (13%) | 11 (85%) | 2 (15%) | 51 (86%) | 8 (14%) |
| | T3 or T4 | 13 (54%) | 11 (46%) | 4 (67%) | 2 (33%) | 17 (57%) | 13 (43%) |
| | | FET P = 0.0008 | | FET P = 0.507 | | FET P = 0.0003 | |
| Any Age | T1a-T1c | 34 (92%) | 3 (8%) | 11 (85%) | 2 (15%) | 45 (90%) | 5 (10%) |
| | T2a-T2c | 71 (81%) | 17 (19%) | 28 (88%) | 4 (12%) | 99 (83%) | 21 (17%) |
| | T3 or T4 | 33 (70%) | 14 (30%) | 11 (85%) | 2 (15%) | 44 (73%) | 16 (27%) |
| | | FET P = 0.049 | | FET P = 1.000 | | FET P = 0.081 | |

In this Table row percents denote the proportion of each stage tumor in each genotype class. FET was determined by a two-tailed Fisher's Exact Test. "W" stands for CYP3A4-W having a wild-type regulatory region while "V" stands for CYP3A4-V having a variant regulatory region.

As shown in Table 1, CYP3A4-V genotypes were more common in higher stage tumors (FET P-value=0.081; $\chi^2_1$=5.12, p=0.024), and there were significant differences in this relationship by family history and age at diagnosis ($\chi^2_{CMH}$=4.91, df=1, P=0.027). No association of CYP3A4 with stage in family history positive or early diagnosis tumors were observed, possibly due to sample sizes. However, there was a significant effect of genotype in later age at diagnosis tumors (FET P-value=0.0003; $\chi^2_1$=14.8 1, P<0.001), family history negative tumors (FET P-value=0.049; $\chi^2_1$=6.12, P=0.013), or tumors that were both later age at diagnosis and family history negative (FET P-value=0.0008; $\chi^2_1$=12.28, P<0.001). Age- and detection method-adjusted odds ratios from polytomous logistic regression approximated the relative risk of having an advanced stage (T3/T4) tumor associated with the CYP3A4-V genotype to be 2.10 (95% confidence interval [CI]=1.09–4.05). The adjusted odds ratio estimates increased to 2.72 (95% CI=1.24–5.61) for family history negative patients, 6.70 (95% CI=2.54–17.69) for later age at diagnosis patients, and 9.45 (95%

CI=2.54–35.17) for both family history negative and later age at diagnosis patients, respectively.

By collapsing stage data in Table 1, the effect of genotype on nonpalpable (stage T1) and palpable (stages T2–T4) tumors was also evaluated. A marginally significant relationship between CYP3A4-V and palpable disease remained in family history negative patients (FET P-value=0.060; $\chi^2_1$=4.02, P=0.045) and a significant association remained with later age at diagnosis patients (FET P-value=0.023; $\chi^2_1$=5.29, P=0.021). The adjusted odds ratio estimates in these groups were 4.42 (95% CI=1.17–16.63) for family history negative patients and 8.34 (95% CI=1.06–65.58) for patients with a later age at diagnosis, respectively. No relationship with genotype was observed in other patient groups. This may be explained in part by small sample sizes in some groups. In all analyses, identical inferences were obtained when the data were stratified using age cutpoints other than the median (e.g., $\leq$60, >60; $\leq$65, >65).

CYP3A4-V genotype was also over represented in patients with higher Gleason grade tumors with no family history who were diagnosed at a later age. In this group, 13% of patients whose tumors had a Gleason grade of six or less carried CYP3A4-V, compared with 24% of patients whose tumors were Gleason grade seven or greater ($\chi^2_1$=16.73, P=0.010). However, no significant effect of CYP3A4 genotype on Gleason grade was detected in the total sample, and there was no difference in the genotype-specific mean Gleason grade in any age or family history-specific group. As shown in Table 2, CYP3A4 genotype distinguished tumors defined simultaneously by stage and grade in later age at diagnosis patients (FET P-value=0.035; $\chi^2_1$=4.64, P=0.031), and marginally significantly in family history negative patients (FET P-value=0.074; $\chi^2_1$=3.36, P=0.067), but not in other groups.

TABLE 2

Association of CYP3A4 Genotype with Combined Gleason Grade and TNM Stage in 230 Incident Prostate Cancer Patients

| Age of Diagnosis | Grade or Stage | Family History Negative | | Family History Positive | | Any Family History | |
|---|---|---|---|---|---|---|---|
| | | W | V | W | V | W | V |
| $\leq$63 years | Low | 15 (88%) | 2 (12%) | 4 (67%) | 2 (33%) | 19 (83%) | 4 (17%) |
| | High | 69 (79%) | 18 (21%) | 25 (93%) | 2 (7%) | 94 (82%) | 20 (18%) |
| | | FET P = 0.516 | | FET P = 0.142 | | FET P = 1.000 | |
| >63 years | Low | 11 (100%) | 0 (0%) | 5 (100%) | 0 (0%) | 16 (100%) | 0 (0%) |
| | High | 43 (75%) | 14 (25%) | 16 (80%) | 4 (20%) | 59 (77%) | 18 (23%) |
| | | FET P = 0.103 | | FET P = 0.549 | | FET P = 0.035 | |
| Any Age | Low | 26 (93%) | 2 (7%) | 9 (82%) | 2 (18%) | 35 (90%) | 4 (10%) |
| | High | 112 (78%) | 32 (22%) | 41 (87%) | 6 (13%) | 153 (80%) | 38 (20%) |
| | | FET P = 0.074 | | FET P = 0.639 | | FET P = 0.179 | |

Again, identical inferences were obtained when analyses were undertaken using age cutpoints other than the median. Thus, the effect of CYP3A4 is believed to be greater on tumor stage than on Gleason grade.

The pronounced effect of CYP3A4 genotype on clinical presentation of prostate cancer in men diagnosed at an older age is believed to be associated with increased testosterone bioavailability resulting from the CYP3A4-V genotype. In aging men, there is a moderate decline in free testosterone levels and a possible shift in the distribution of testosterone metabolites. It is believed that increased testosterone bioavailability associated with CYP3A4-V is relatively more important in older men with lower basal testosterone levels as compared with younger men who have higher basal testosterone levels.

CYP3A4 genotypes are also associated with the significant differences in CYP3A4 metabolism and rates of prostate cancer which occur across ethnic groups. The frequency of the CYP3A4 variant was estimated in three ethnic groups with different prostate cancer incidence rates. The CYP3A4-V allele frequency was estimated to be 0.53 in African Americans (heterozygosity=0.51), 0.09 in U.S. Caucasians (heterozygosity=0.10) and 0 in Taiwanese (no CYP3A4-V was observed on 260 chromosomes) using CSGE analysis. There were significant differences among genotype frequencies across the three racial groups (p<0.0001). CYP3A4 genotype frequencies were significantly higher in African Americans compared with U.S. Caucasians (p<0.0001), in U.S. Caucasians compared with Taiwanese (p<0.0001), and African Americans compared with Taiwanese (p<0.0001).

Two additional analyses were undertaken to further evaluate CYP3A4-V. First, 79 subjects were typed by both CSGE and LCR. The LCR approach had a sensitivity of 90% relative to CSGE and direct sequencing, and confirmed the existence of CYP3A4-V using an independent assay. Second, CYP3A4-V detection was undertaken in 43 members of a five generation African American family using the CSGE assay. These analyses demonstrated that CYP3A4 alleles segregated in a Mendelian manner. Seven of 16 (44%) biologically unrelated "marry-ins" carried CYP3A4-V. Accordingly this variant is common in African Americans. The differences in CYP3A4-V frequency by ethnicity correspond to the relative 1992 age-adjusted incidence rates of prostate cancer in African Americans (180.6 per 100,000; Miller et al. Nat. Cancer Inst. NIH Pub No. 96-4104, Bethesda, Md., 1996), Caucasians (134.7 per 100,000; Miller et al. Nat. Cancer Inst. NIH Pub No. 96-4104, Bethesda, Md., 1996) and Taiwanese 5.7 per 100,000 (Department of Health Executive Yuan 1996).

The identification of CYP3A4 as a biomarker associated with prostate cancer has implications for treatment and prevention of prostate cancer. Knowledge about CYP3A4 provides useful information about prostate cancer treatment and prognosis. Since CYP3A4 enzyme is detectable in only 61% of prostate tumors, it is believed that there is tumor-specific variability in CYP3A4 expression. Further, it is believed that response to hormone therapy is in part determined by CYP3A4 genotype and/or CYP3A4 phenotype. The fact that stage at diagnosis is associated with genotype also indicates that knowledge of CYP3A4 is valuable in evaluating prognosis, since prostate tumor stage is an important predictor of prostate cancer mortality.

Thus, the present invention relates to a method of identifying patients with heightened risk of developing or having prostate cancer. In this method, a biological sample is obtained from the patient. Any biological sample containing DNA of the patient can be used. The sample is then tested for the presence of a nucleic acid sequence encoding a CYP3A4 variant. The presence of this variant is indicative of a heightened risk of the patient developing or having prostate cancer.

The present invention also relates to methods of enhancing treatment of primary prostate cancer by knowledge about CYP3A4 genotype. For example, in addition to its effects on testosterone metabolism, CYP3A4 also oxidizes finasteride, an inhibitor of the 5α-reductase involved in formation of DHT. Since individuals who carry CYP3A4-V are believed to have increased activity in the testosterone-DHT pathway, CYP3A4 genotype can influence an individual's response to prostate cancer chemoprevention by finasteride. Thus, more effective treatment regimes can be identified for patients suffering from prostate cancer by identifying those patients suffering from prostate cancer who carry a variant CYP3A4 gene and selecting a treatment regime which is more effective in the presence of the variant CYP3A4 gene.

This polymorphism in the 5' promoter region of the CYP3A4 gene (CYP3A4-V) is also believed to alter the metabolism of anticancer drugs and to possibly decrease the production of DNA damaging metabolites from anticancer drugs which cause treatment-related leukemias in some patients.

Ninety-nine de novo and 30 treatment-related leukemias were examined using a conformation-sensitive gel electrophoresis assay for the presence of the CYP3A4-V. In all treatment-related cases, there was prior exposure to one or more anticancer drugs metabolized by CYP3A. Nineteen of 99 (19%) de novo and 1 of 30 treatment-related leukemias (3%) carried CYP3A4-V (p=0.026, Fisher's Exact Test). Nine of 42 (21%) de novo leukemias with MLL gene translocations and 0 of 22 treatment-related leukemias with MLL gene translocations carried CYP3A4-V (p=0.016, Fisher's Exact Test). This relationship remained significant when 19 treatment-related leukemias with MLL gene translocations that followed epipodophyllotoxin exposure were compared with the same 42 de novo cases (FET p value= 0.026). These data indicate that individuals with CYP3A4-W genotype have an increased risk for developing treatment-related leukemia and that epipodophyllotoxin metabolism by CYP3A4 may contribute to the secondary cancer risk. The CYP3A4-W genotype is believed to increase production of potentially DNA damaging reactive intermediates. The variant is believed to decrease production of the epipodophyllotoxin catechol metabolite, which is precursor of the potentially DNA-damaging quinone.

Table 3 describes the molecular, demographic, and clinical characteristics of all four groups of subjects (n=129).

TABLE 3

Characteristics of 129 Subjects with Leukemia

| | de novo | | | Treatment-related | | | |
|---|---|---|---|---|---|---|---|
| | Grp 1 11q23 (42) | Grp 3 Non-11q23 (57) | Total (99) | Grp 2 11q23 (22) | Grp 4 Non-11q23 (8) | Total (30) | Total (129) |
| Age at DX: Mean, (SD), {n} | 2.2, (5.1), {42} | 7.7, (5.4), {49} | | 11.2, (4.7), {22} | 14.1, (8.8), {8} | | |
| Male | 16 (38%) | 37 (65%) | 53 (53%) | 13 (59%) | 3 (38%) | 16 (53%) | 69 (53%) |
| Female | 26 (62%) | 19 (33%) | 45 (45%) | 9 (41%) | 5 (63%) | 14 (47%) | 59 (46%) |
| NA | 0 | 1 (2%) | 1 (1%) | 0 | 0 | 0 | 1 (1%) |
| Caucasian | 37 (88%) | 36 (63%) | 73 (74%) | 19 (86%) | 6 (75%) | 25 (83%) | 98 (76%) |
| Black | 3 (7%) | 9 (16%) | 12 (12%) | 0 | 0 | 0 | 12 (9%) |
| Hispanic | 2 (5%) | 3 (5%) | 5 (6%) | 3 (14%) | 1 (13%) | 4 (13%) | 9 (7%) |
| Asian | 0 | 2 (4%) | 2 (2%) | 0 | 0 | 0 | 1 (2%) |
| NA | 0 | 7 (12%) | 7 (7%) | 0 | 1 (13%) | 1 (3%) | 8 (6%) |
| ALL | 21 (50%) | 57 (100%) | 78 (79%) | 3 (14%) | 0 | 3 (10%) | 81 (63%) |
| AML | 18 (43%) | 0 | 18 (18%) | 16 (73%) | 4 (50%) | 20 (67%) | 38 (29%) |
| Biphenctypic | 3 (7%) | 0 | 3 (3%) | 1 (5%) | 0 | 1 (3%) | 4 (3%) |
| MDS | 0 | 0 | 0 | 2 (9%) | 4 (50%) | 6 (20%) | 6 (5%) |
| FAB L1 | 14 (33%) | 33 (58%) | 47 (47%) | 3 (13%) | 0 | 3 (10%) | 50 (39%) |
| FAB L2 | 3 (7%) | 9 (16%) | 12 (12%) | 0 | 0 | 0 | 12 (9%) |
| FAB M1 | 2 (5%) | 0 | 2 (2%) | 1 (5%) | 0 | 1 (3%) | 3 (2%) |
| FAB M2 | 2 (5%) | 0 | 2 (2%) | 2 (9%) | 0 | 2 (7%) | 4 (3%) |
| FAB M4 | 4 (9%) | 0 | 4 (4%) | 11 (50%) | 2 (25%) | 13 (43%) | 17 (13%) |
| FAB M5 | 10 (24%) | 0 | 10 (10%) | 2 (9%) | 1 (13%) | 3 (10%) | 13 (10%) |
| FAB M6 | 0 | 0 | 0 | 0 | 1 (13%) | 1 (3%) | 1 (1%) |
| FAB M7 | 0 | 0 | 0 | 1 (5%) | 0 | 1 (3%) | 1 (1%) |
| RAEB | 0 | 0 | 0 | 0 | 1 (13%) | 1 (3%) | 1 (1%) |
| RAEB-t | 0 | 0 | 0 | 0 | 1 (13%) | 1 (3%) | 1 (1%) |
| NA | 7 (17%) | 15 (26%) | 22 (22%) | 2 (9%) | 2 (25%) | 4 (13%) | 26 (20%) |
| Survival (mo):Mean, [SD], (range), {n} | 20.4 [19.0] (0.7–71.1) {39} | 37.9 [30.3] (6–125) {49} | | 10.4 [10.5] (0.1–42) {20} | 6.6 [5.8] (0.3–15) {8} | | |
| Interval (mo) : Mean, [SD], (range), {n} | not applicable | not applicable | | 40.5 [31.4] (11–132) {22} | 55.3 [34.8] (14.113) {8} | | |

NA is not available; ALL, acute lymphoblastic leukemia; AML, acute myeloid leukemia; MDS, myelodysplastic syndrome; FAB, the French-American-British classification of morphology; {n}, number of subjects for whom information was available. Survival is from diagnosis of de novo or treatment-related leukemia. Interval is from diagnosis of primary cancer to diagnosis of treatment-related leukemia.

Among the four groups examined, there were significant differences in distribution of age at initial diagnosis (Kruskal-Wallis $\chi^2_1$=52.92, p<0.0001) and gender (FET P-value=0.034), but not race (FET P-value=0.170). Of the 22 Group 2 subjects, 14 (64%) were exposed to cyclophosphamide (CPM), 7 (32%) to ifosphamide (IFOS), 1 (5%) to vinblastine (VBL), 2 (9%) to teniposide (VM26), and 17 (77%) to etoposide (VP16). The regimens contained one CYP3A4 substrate in 7 cases and 2 or 3 CYP3A4 substrates in the other cases. Of the 8 Group 4 subjects, 6 (75%) were exposed to CPM, 5 (63%) to IFOS, 1 (13%) to VBL, none were exposed to VM26, and 6 (75%) were exposed to VP16. The chemotherapy included more than one drug metabolized by CYP3A4 in 7 of 8 cases.

The karyotypes in all treatment-related leukemias were examined for the presence of both copies of chromosome band 7q22, the genomic region encoding CYP3A4 (Inoue et al. Jpn J. Hum. Genet. 1992 37:133–138). The karyotypes indicated that both copies were present in a significant proportion of the cells and that both CYP3A4 alleles would be amplifiable from the leukemic samples.

Significant differences were observed in CYP3A4 genotype distribution among the four groups of subjects. As shown in Table 4, there was a significant deficit of CYP3A4-V genotypes among all treatment-related cases (3%) compared with all de novo cases (19%; FET P-value= 0.026). The age, gender and race-adjusted odds ratio for this association was 0.07 (95% CI: 0.01–0.68). When the analysis was limited to leukemias with MLL gene translocations, no CYP3A4-V genotypes were found in the treatment-related cases in Group 2 compared with 21% of the de novo cases in Group I (FET P-value=0.016). Because none of the 22 Group 2 subjects carried the CYP3A4-V, no odds ratio could be estimated. Three Group 2 subjects did not have prior exposure to epipodophyllotoxin. After removal of these cases and analysis of epipodophyllotoxin-exposed Group 2 subjects, the observation that CYP3A4-V was under represented in treatment-related leukemias with MLL gene translocations remained significant (FET P-value= 0.026).

TABLE 4

Association of CYP3A4 Genotype with Leukemia Subsets

| Group | Genotype Frequency (Row %) | | FET P-value | OR (95% CI) |
|---|---|---|---|---|
| All de novo cases (Groups 1,3) | 80 (81%) | 19 (19%) | 0.026 | 0.09 (0.01–0.087) |
| All treatment-related cases (Groups 2,4) | 29 (97%) | 1 (3%) | | |
| de novo 11q23 (Group 1) | 33 (79%) | 9 (21%) | 0.016 | c |
| Treatment related 11q23 (Group 2) | 22 (100%) | 0 (0%) | | |
| de novo 11q23 (Group 1) | 33 (79%) | 9 (21%) | 0.026 | c |
| Epipodophyllo-toxin-related 11q23 (Group 2 subset) | 19 (100%) | 0 (0%) | | |
| All 11q23 (Groups 1,2) | 55 (86%) | 9 (14%) | 0.419 | 1.33 (0.42–4.20) |
| All non-11q23 (Groups 3,4) | 54 (83%) | 11 (17%) | | |
| de novo non-11q23 (Group 3) | 47 (82%) | 10 (18%) | 0.592 | 0.37 (0.02–4.59) |
| Treatment-related non-11q23 (Group 4) | 7 (88%) | 1 (12%) | | |
| Treatment-related 11q23 (Grcup 2) | 22 (100%) | 0 (0%) | 0.267 | c |
| Treatment-related non-11q23 (Group 4) | 7 (88%) | 1 (12%) | | |

Odds ratio and 95% CI were adjusted by multiple logistic regression for age at diagnosis of leukemia, race, gender and survival time. "c" represents odds ratio and 95% CI which can not be estimated due to zero cells.

To evaluate whether the genotype effect was specific to treatment-related leukemias with MLL gene translocations, CYP3A4 genotype in patients with de novo and treatment-related leukemias without MLL gene translocations (Groups 3 and 4) were also determined. No difference was observed (FET P-value=0.592).

Because differences in survival times can affect the chances of developing treatment-related leukemia, it was also determined whether the mean survival time from diagnosis in patients with de novo leukemia in Groups 1 and 3 was similar to the mean interval from primary cancer diagnosis to development of treatment-related leukemia in Groups 2 and 4. The mean survival time in Groups 1 and 3 was 30.1 months; the mean interval from primary cancer diagnosis to development of treatment-related leukemia in Groups 2 and 4 was 44.4 months (Table 3). Since this difference was significant ($F_{1,88}$ from ANOVA=5.56, P-value=0.02), the association analyses was adjusted for total duration of follow up. The resulting odds ratio association comparing all de novo cases against all treatment-related cases (OR=0.09, 95% CI: 0.01–0.87) was not substantially different from the analyses adjusted only for age at diagnosis, race and gender, indicating that the effect of CYP3A4 genotype remained significant even after adjustment for different follow-up times among case groups.

DNA topoisomerase II inhibitors, especially the epipodophyllotoxins, are associated with treatment-related leukemias in about 2% of patients. Molecular cancer epidemiology has not identified specific mutations that confer genetic susceptibility or mutagen sensitivity in this form of leukemia. Epipodophyllotoxins, cyclophosphamide, ifosphamide, vinblastine and vindesine all are substrates for CYP3A (Li et al. Toxicology 1995 104:1–8; Relling, M. Am. Soc. Pharmacol. Exp. Therapeut. 1994 45:352–358). As demonstrated in these studies, a significant deficit of the CYP3A4-V was observed among subjects who developed treatment-related leukemia following chemotherapeutic agents metabolized by CYP3A.

These results indicate that CYP3A4-W is associated with chemotherapy effects, particularly epipodophyllotoxin effects, leading to MLL gene translocations. Conversely, these results also indicate that CYP3A4-V is less frequently associated with DNA damage leading to MLL gene translocation as a separate subgroup. A significant relationship was observed with CYP3A4 genotype in this patient subset. The deficit of CYP3A4 genotype may also be associated with alkylating agent-induced leukemia.

CYP3A4 catalyzes O-demethylation of the epipodophyllotoxin dimethoxyphenol E ring to form the catechol metabolite. The catechol is precursor to a quinone metabolite, which has been suggested to produce depurinating N7-guanine adducts (Cavalieri et al. Proc. Natl Acad. Sci. USA 1997 94:10937–10942). Such adducts are believed to result in the formation of abasic sites in DNA from the action of DNA glycosylases (Demple, B. and Harrison, L. Annu. Rev. Biochem. 1994 63:915–948; Sun et al. J. Biol. Chem. 1995 270:19501–19508; Singer, B. and Hang, B. Chem Res. Toxicol. 1997 10:713–732; and Krokan et al. Biochem. J. 1997 325:1–16). While enhanced DNA topoisomerase II cleavage is the mechanism of chromosomal breakage from epipodophyllotoxin parent drugs, abasic sites at critical positions in the DNA increase DNA topoisomerase II cleavage much more than the parent drugs (Kingma et al. J. Biol. Chem. 1995 270:21441–21444; Kingma, P and Osheroff, N. J. Biol. Chem. 1997 272:1148–1155; Kingma, P. and Osheroff, N. J. Biol. Chem. 1997 272:7488–7493; and Kingma et al. Biochem. 1997 36:5934–5939). Unrepaired DNA adducts result in recruitment of recombinational repair when there is blockage of the replication fork. Redox cycling of the catechol and quinone metabolites generates reactive oxygen species and hydroxyl radicals that are believed to cause oxidative damage to the DNA. This oxidative DNA damage can generate interstrand crosslinks that recruit recombinational repair. Thus, epipodophyllotoxin catechol and quinone metabolites have potential genotoxic properties of relevance to translocations.

Thus, CYP3A4-V is a genotypic factor that modulates leukemogenic drug effects. It is believed that CYP3A4-V, which disrupts a regulatory element 5' to the CYP3A4 gene, may be associated with decreased CYP3A4 expression or decreased activity of the enzyme. Further, it is believed that this decrease in expression or activity of CYP3A4 may reduce formation of genotoxic metabolites in individuals carrying CYP3A4-V. Conversely, CYP3A4-W may be associated with increasing metabolism of epipodophyllotoxins to the corresponding catechol which, via redox cycling, forms the DNA-damaging quinone. Accordingly, patients identified as carriers of CYP3A4-W are at higher risk for development of treatment-related leukemias, and in particular leukemias resulting from administration of epipodophyllotoxins. Patients can therefore be screened prior to administration of an anticancer agent to identify those carrying CYP3A4-W and CYP3A4-V so that a treatment regime based on the genotype can be used. For example, a treatment other than administration of an epipodophyllotoxin may be preferred for patients carrying CYP3A4-W.

Thus, the present invention also relates to methods of identifying patients at risk for developing treatment-related leukemia upon administration of an epipodophyllotoxin. In this method, a biological sample is obtained from the patient. Any DNA containing sample obtained from the patient can serve as the biological sample. The sample is then tested for the presence of a nucleic acid sequence encoding either wild-type CYP3A4 or a variant of CYP3A4. The presence of wild-type CYP3A4 is indicative of an increased risk of the patient developing treatment-related leukemia upon administration of an epipodophyllotoxin while the presence a variant of CYP3A4 is indicative of a decreased risk of the patient developing treatment-related leukemia upon administration of an epipodophyllotoxin.

Various methods for screening biological samples for the presence of a selected nucleic acid sequence such as CYP3A4-W or CYP3A4-V are well known in the art. In one embodiment, as described herein in Example 2, PCR amplification is used to detect CYP3A4 in the sample. However, as will be obvious to those of skill in the art upon this disclosure, other methods such as PCR coupled with restriction fragment polymorphism analysis by gel electrophoresis can also be used.

Also provided in the present invention are kits for determining the CYP3A4 genotype of a patient. These kits comprise a means for detecting variant or wild-type CYP3A4 in a biological sample. In a preferred embodiment, the kit comprises primer pairs for detection of a variant CYP3A4 via PCR amplification. An example of a primer pair which can be incorporated into the kit of the present invention comprises 5'-AAC AGG CGT GGA AAC ACA AT-3' (SEQ ID NO:5) and 5'-CTT TCC TGC CCT GCA CAG-3' (SEQ ID NO:6). Kits of the present invention are useful in identifying patients with heightened risk of developing or having prostate cancer and patients at risk for developing treatment-related leukemia upon administration of an epipodophyllotoxin.

The following nonlimiting examples are provided to further illustrate the present invention.

EXAMPLES

Example 1

Sample Subjects and Biosample Collection for Studies of Prostate Cancer

A reference panel (N=94) consisting of healthy, unrelated, Caucasian, male volunteers with no history of cancer at any site was assembled. This panel was used to identify variants in CYP3A4. The mean age of these men was 63.4 years (standard deviation [SD]=12.3 years; range: 23–89 years). A sample of 230 patients representing incident prostate cancer cases was also identified. Because of small numbers in other ethnic groups, only non-Hispanic, Caucasian men were included in this study. Men were excluded from this study if they had any history of exposure to finasteride (Proscar) at the time of their prostate cancer diagnosis. Patients who were nonincident cases (i.e., those diagnosed more than twelve months prior to the date of study ascertainment) were also excluded. The mean age of diagnosis was 63.3 years (SD=7.8 years) with a range of 45–90 years.

Genomic DNA was self-collected by each study subject using sterile cheek swabs (Cyto-Pak Cytosoft Brush, Camarillo, Calif.), and processed using a protocol modified from Richards et al. (Hum. Mol. Genet. 1993 2(2):159–163). In this procedure, the swab brush was placed inside a 1.5 mL microcentrifuge tube, and 600 $\mu$L of 50 mM NaOH was added. The closed tube was vortexed for 5 minutes, and then heated at 95° C. for 10 minutes. Finally, 120 $\mu$L of 1 M Tris (pH 8.0) was added, after which the brush was removed and discarded.

Clinical characteristics at diagnosis were obtained by medical records abstraction. These characteristics included clinical and pathologic Gleason grade (Gleason D. F. The Veteran's Administration Cooperative Urologic Research group: histologic grading and clinical staging of prostatic carcinoma. In: Tannenbaum M (ed.) Urologic Pathology: The Prostate, pp. 171–198. Philadelphia: Lea and Febiger, 1977), prostate specific antigen (PSA) levels at diagnosis, and TNM (Beahrs et al. (eds.): Manual for Staging of Cancer, 4th edition, pp. 185–186. Philadelphia: J B Lippincott, 1992) tumor stage. One hundred forty five (63%) subjects underwent radical prostatectomy for treatment of their disease. Tumor stage and grade were determined by histopathologic review in these cases, which described the capsular status, percent tumor volume, and seminal vesicle involvement. Tumors from the remaining 85 patients were staged by a combination of serum PSA, digital rectal examination, bone scan, and endorectal magnetic resonance imaging. Of the 13 patients with T3c stage tumors, eight were based only on PSA, digital rectal examination, magnetic resonance imaging, and bone scan alone, while five also underwent seminal vesicle biopsy. Pathologic grading using the Gleason system was undertaken after 6–11 transrectal ultrasound-guided needle biopsies. Diagnoses originally made at other institutions underwent reinterpretation of the original biopsy material at HUP. For analysis, three TNM stage variables were considered. First, sstages T1a–T1c (denoted T1), T2a–T2c (denoted T2), and T3/T4 were considered. Second, a binary stage variable of non-palpable (Stages T1a–T1c) and palpable disease (Stages T2a–c, 3a–c, and 4a–b) was considered. Finally, a combined disease classification defined simultaneously by stage and grade, in which tumors of stages T1a–c and a Gleason grade less than 7 were compared with tumors of stages T2–T4 or T1 and a Gleason grade less than 7, was considered. Additional risk factor information was obtained by self report using a questionnaire. These variables included demographic characteristics, exposure history, medical history, and family history of prostate cancer.

Example 2
CYP3A4 Genotype Analysis

Detection of variant alleles was accomplished by PCR amplification of a 592 base pair (bp) fragment upstream from CYP3A4 and including a portion of exon 1 (nucleotides −571 to +22). The primers used in this amplification (5'-AAC AGG CGT GGA AAC ACA AT-3' (SEQ ID NO:5) and 5'-CTT TCC TGC CCT GCA CAG-3' (SEQ ID NO:6)) were generated from the published CYP3A4-specific nucleotide sequence of Hashimoto et al. (Eur. J. Biochem. 1993 218:585–595). The PCR reaction mixture consisted of 10 μL double distilled $H_2O$, 5 μL 10×PCR Buffer (Perkin-Elmer Corp., Foster City, Calif.), 3 μL 25 mM $Mg^{+2}$, 1 μl 10 mM dNTP's, 5 μL each of 5 mM PCR Primers, 10 μL of template DNA, 0.8 μL Taq polymerase (Amplitaq, Perkin-Elmer), and 12.2 μL double distilled $H_2O$, for a total volume of 50 μL. The temperature profile for the PCR reaction was one cycle each of 94° for 5 minutes, 82° for 1 minute, followed by 25 cycles of 94° for 1 minute, 66 cycles for 1 minute with a 0.5°/cycle decrease, and 72° for 1 minute. This was followed by eight cycles of 94° for 1 minute, 50° for 1 minute, 72° for 1 minute, and a final single 72° cycle for 10 minutes.

Genotypes were visualized by conformation-sensitive gel electrophoresis (CSGE) of the PCR product on a 10% non-denaturing polyacrylamide gel using the protocol of Ganguly et al. (Proc. Natl Acad. Sci. USA 1993 90:10325–10329), after staining with ethidium bromide. To identify homozygous wild-type (W/W), homozygous variant (V/V), and heterozygous (W/V) genotypes using CSGE, two samples were loaded onto the polyacrylamide gel for each subject. In one well, a 6 μL PCR sample was loaded with 6 μL of PCR-generated homozygous variant (V/V) DNA from a known V/V subject (denoted '+V/V'). In a second well, a 12 μL PCR sample was loaded onto the gel without the addition of V/V DNA (denoted '−V/V'). In V/V subjects, a single (homoduplex) band was always observed. In W/V subjects, homoduplex and heteroduplex bands were always observed. Thus, the addition of V/V DNA had no effect on the banding pattern for V/V and W/V subjects. In W/W subjects, a single (homoduplex) band was present in those lanes without V/V DNA. The addition of known V/V DNA to the DNA of subjects with W/W genotypes produced both homoduplex and heteroduplex bands.

Example 3
Statistical Methods in Prostate Cancer Studies

Analyses were undertaken using non-parametric methods to compare proportions in contingency tables using two-sided Fisher's exact tests (FETs) and/or Kruskal-Wallis $\chi^2$ statistics (for analysis of continuous variables such as PSA level or Gleason grade). Odds ratios were estimated using logistic regression models for polytomous or binary outcome stage or grade data. All odds ratio estimates were adjusted for age at diagnosis and method of prostate cancer detection. Detection method was coded as three binary (yes/no) covariates describing referral for diagnosis because of elevated PSA, abnormal digital rectal examination at routine screening, and/or the existence of prostate cancer symptoms. Stratified analyses were undertaken to compare genotype effects by family history and age at diagnosis. Positive family history was defined as having at least one first or second degree relative with prostate cancer. Using this definition, 25% of patients had a positive family history of prostate cancer. Therefore, an individual in this study defined as having a positive family history of prostate cancer did not necessarily come from a family with a hereditary pattern of prostate cancer. Age at diagnosis was stratified at the sample's median age of diagnosis (63 years) to distinguish "earlier age at diagnosis" patients (i.e., those diagnosed at or before 63 years of age) and from "later age at diagnosis" patients (i.e., those diagnosed after 63 years of age). The Cochran Mantel Haenszel chi square test ($\chi^2_{CMH}$) for nonzero correlation among strata was used to compare contingency tables stratified by family history and/or age at diagnosis.

Example 4
Subjects and Biosamples from Patients with Leukemia

Genomic DNAs and clinical information were obtained on patients with a diagnosis of leukemia. The patients were grouped according to whether the leukemia was de novo or followed prior anticancer treatment and whether the leukemia was characterized by translocation of the MLL gene at chromosome band 11q23. Genomic DNA was isolated from leukemic marrow or peripheral blood mononuclear cells as previously described, and Southern blot analysis was used to identify MLL gene rearrangements (Felix et al. Blood 1997 90:4679–4686; and Megonigal et al. Proc. Natl Acad. Sci. USA 1998 95:6413–6418). Group 1 included 42 patients with de novo leukemia s characterized by molecular translocation of the MLL gene. Group 2 included 22 patients with treatment-related leukemias characterized by molecular translocation of the MLL gene, although in 5 cases this was not cytogenetically apparent. All received prior chemotherapy with at least one agent metabolized by CYP3A4 (Li et al. Toxicology 1995 104:1–8). Exposures included etoposide, teniposide, cyclophosphamide, ifosphamide or vinblastine. In all Group 1 and Group 2 cases, MLL gene rearrangement was within the breakpoint cluster region (bcr) except in a single Group I case, where the rearrangement mapped 5' of the bcr between MLL intron 3 and exon 5 (Felix et al. Blood 1995 85:3250–3256).

The 57 patients in Group 3 were diagnosed with de novo B-lineage ALL and were studied as a control population with a common pediatric cancer. MLL gene rearrangement was excluded in all cases by Southern blot analysis of BamHI digested DNA with the B859 cDNA probe from the MLL breakpoint cluster region (Gu et al. Cell 1992 71:701–708). Group 4 included 8 patients with treatment-related leukemia without cytogenetic and/or molecular evidence of translocation of chromosome band 11q23. In all 8 cases, there was a prior cancer diagnosis and a history of exposure to at least one anticancer drug metabolized by CYP3A4.

Clinical and demographic features, karyotypes and rearranged or germline MLL gene configuration in 30 Group 1 patients (Felix et al. Blood 1997 90:4679–4686; and Megonigal et al. Proc. Natl. Acad. Sci. USA 1998 95:6413–6418), 11 Group 2 patients (Felix et al. Blood 1996 87:4376–4381; Felix et al. Blood 1995 85:3250–3256; Megonigal et al. Proc. Natl Acad. Sci. USA 1997 94:11583–11588) and 2 Group 4 patients (Felix et al. Blood 1996 87:4376–4381; Felix et al. Blood 1995 85:3250–3256), and clinical and demographic features in 27 Group 3 patients (Felix et al. J. Clin. Oncol. 1990 8:431–442) have been described.

Example 5
CYP3A4 Genotype Determination

Genomic DNA was available from bone marrow or peripheral blood at either diagnosis or relapse of leukemia. Genotypes were examined by PCR amplification of a 592 bp template from upstream of the CYP3A4 gene extending into exon I (nucleotides −571 to +22), and analysis of the products in a conformation-sensitive gel electrophoresis (CSGE) assay as described in Example 2.

Example 6
Statistical Methods in Leukemic Patients

Proportions in contingency tables were compared by non-parametric methods. Fisher's Exact Test (FET) was used for analysis of contingency tables with less than 5 observations per cell. Odds ratios were estimated using logistic regression models for binary outcome data and were adjusted for age at diagnosis, race and gender. All analyses were performed using SAS version 6.11 statistical software.

What is claimed is:

1. A nucleic acid sequence encoding a variant of CYP3A4 comprising SEO ID NO:2.

2. A method of identifying patients with heightened risk of developing or having prostate cancer comprising:
   (a) obtaining a biological sample from a patient; and
   (b) testing the biological sample for the nucleic acid sequence of claim 1, wherein the presence of the nucleic acid sequence is indicative of a heightened risk of the patient developing or having prostate cancer.

3. A method of identifying patients at risk for developing treatment-related leukemia upon administration of an epipodophyllotoxin comprising:
   (a) obtaining a biological sample from a patient; and
   (b) identifying whether the patient carries CYP3A4-W or a nucleic acid of claim 1, wherein the presence of CYP3A4-W is indicative of an increased risk of the patient developing treatment-related leukemia upon administration of an epipodophyllotoxin while the presence of the nucleic acid sequence of claim 1 is indicative of a decreased risk of the patient developing treatment-related leukemia upon administration of an epipodophyllotoxin.

4. A kit for detecting a CYP3A4 variant in a biological sample which comprises a means for detecting the nucleic acid sequence of claim 1.

5. The kit of claim 4 wherein the nucleic acid sequence is detected by PCR amplification using a primer comprising SEQ ID NO: 5 and 6.

6. A method for identifying more effective treatment regimes for prostate cancer comprising:
   (a) identifying individuals suffering from prostate cancer who carry a variant CYP3A4 gene comprising SEO ID NO:2; and
   (b) selecting a treatment regime which is more effective in the presence of the variant CYP3A4 gene.

7. A method of selecting safer anticancer treatments for patients suffering from cancer comprising:
   (a) identifying patients carrying wildtype CYP3A4; and
   (b) selecting a treatment regime other than an epipodophyllotoxin for patients identified as carrying wildtype CYP3A4.

* * * * *